United States Patent [19]

Meilland, deceased

[11] Patent Number: Plant 6,818

[45] Date of Patent: May 30, 1989

[54] ROSE PLANT — MEITIFRAN VARIETY

[75] Inventor: Marie-Louise Meilland, deceased, late of Antibes, France, by Jean-Pierre Le Naour, legal representative

[73] Assignee: The Conard-Pyle Company, West Grove, Pa.

[21] Appl. No.: 145,393

[22] Filed: Jan. 19, 1988

[51] Int. Cl.[4] ..... A01H 5/00

[52] U.S. Cl. ..... Plt./7

[58] Field of Search ..... Plt./7

*Primary Examiner*—James R. Feyrer

*Attorney, Agent, or Firm*—Burns, Doane, Swecker & Mathis

[57] ABSTRACT

A new and distinct variety of rose plant of the Miniature Class is provided which forms in abundance highly attractive bicolored very double blossoms. The blossoms are white in coloration and bear bengal rose edges. The plant has glossy foliage, reflowers well, and forms blossoms having an umbrella configuration when fully open. The central petals tend to be tapered and small. The new variety is particularly well suited for use as attractive ornamentation when grown as a flowering pot plant either indoors or outdoors.

1 Drawing Sheet

SUMMARY OF THE INVENTION

The new variety of Miniature rose plant was created by artificial pollination wherein two parents were crossed which previously had been studied in the hope that they would contribute the desired characteristics. The female parent (i.e., the seed parent) was the Magic Carrousel variety (U.S. Plant Pat. No. 3,601). The male parent (i.e., the pollen parent) of the new variety was the product of the pollination of the Alain variety (non-patented) by *Rosa mutabilis* on the one side and the Medar variety (non-patented) by the Caprice variety (non-patented) on the other side. The percentage of the new variety can be summarized as follows:

[Magic Carrousel] × [Alain × *Rosa mutabilis*) × (Medar × Caprice)].

The seeds resulting from the above pollination were sown and 137 plantlets were obtained which were physically and biologically different from each other. Selective study resulted in the identification of a single plant of the new variety.

It was found that the new variety of Miniature rose plant of the present invention possesses the following combination of characteristics:

(a) forms in abundance on a continuous basis attractive very double bicolored blossoms which are white with bengal rose edges, have small central petals, and assume an umbrella configuration when fully open,
(b) exhibits a bushy growth habit, and
(c) forms glossy foliage.

The new variety well meets the needs of the horticultural industry for many usages. It is particularly well-suited for use as attractive ornamentation as a flowering pot plant for use indoors or outdoors.

The new variety has been found to undergo asexual propagation by a number of routes, including budding, grafting, cuttage, etc. The characteristics of the new variety have been found to be strictly transmissible by such asexual propagation from one generation to another.

The new variety has been named the Meitifran variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were two years old and observed during June while growing on their own roots outdoors at Cannet-des-Maures, Var, France.

FIG. 9 illustrates specimens of a pair of fully open flowers immediately prior to petal drop — plan view — reverse;

DETAILED DESCRIPTION

Figures 1, 2, 3, 4, 5, 6, 7, 8, 10, 11, 12, 13, 14, 15, 16:
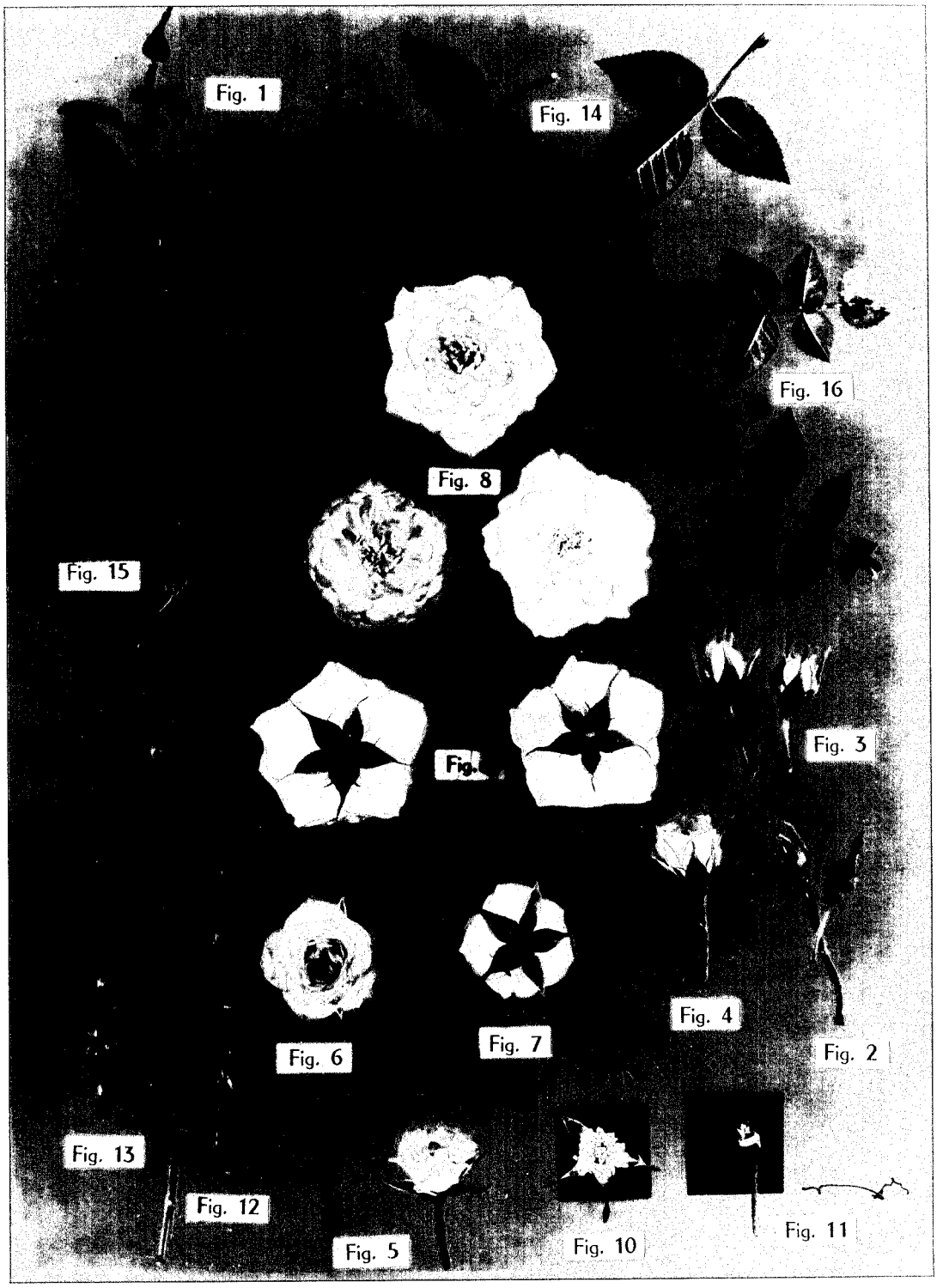
FIG. 1 illustrates a specimen of a young shoot.
FIG. 2 illustrates a specimen of a pair of floral buds before the opening of the sepals.
FIG. 3 illustrates a specimen of a pair of floral buds at the opening of the sepals.
FIG. 4 illustrates a specimen of a floral bud at the opening of the petals.
FIG. 5 illustrates a specimen of a flower in the course of opening.
FIG. 6 illustrates a specimen of a fully open flower — plan view — obverse.
FIG. 7 illustrates a specimen of a fully open flower — plan view — reverse.
FIG. 8 illustrates specimens of three fully open flowers immediately prior to petal drop — plan view — obverse.
FIG. 10 illustrates a specimen of a floral receptacle showing the arrangement of the stamens and pistils.
FIG. 11 illustrates a specimen of a floral receptacle showing the arrangement of the pistils (sepals and stamens removed)
FIG. 12 illustrates specimens of a pair of flowering stems.
FIG. 13 illustrates a specimen of a main branch.
FIG. 14 illustrates specimens of leaves with three leaflets with the upper surface being shown on the left and the under surface being shown on the right.
FIG. 15 illustrates specimens of leaves with five leaflets with the upper surface being shown on the top and the under surface being shown on the bottom.
FIG. 16 illustrates specimens of leaves with seven leaflets with the under surface being shown on the top and the upper surface being shown on the bottom.

The chart used in the identification of the colors is that of The Royal Horticultural Society (R.H.S. Colour Chart). The terminology which precedes the chart information has been added to indicate the colors in common terms. The description is based on the observation of two year old specimens of the new variety during June while growing outdoors on their own roots at Cannet-des-Maures, Var, France.

Class: Miniature.

Plant:

*Height.*—Approximately 25 to 30 cm. on average.

*Habit.*—Bushy.

Branches:

*Color.*—Young stems: light green, Green Group 143C. Adult wood: medium green, Green Group 143B.

Leaves:

*Petioles.*—Upper surface: grooved, light green on young foliage and medium green on adult foliage with glandular edges. Under surface: medium green with some small glandular aciculas.

*Stipules.*—Adnate, pectinate, narrow and linear.

*Leaflets.*—Number: 3, 5 (most often), 7 and 9 sometimes. Shape: lance shaped. Serration: simple and regular. Texture: firm. General appearance: dense and glossy foliage. Color (young foliage): Upper surface: medium green, Green Group 143A. Under surface: light medium green, Green Group 143A, more or less shaded with a reddish tint. Color (adult foliage): Upper Surface: dark green, Yellow-Green Group 147A. Under surface: light medium green, Green Group 138A.

Inflorescence:

*Number of flowers.*—Approximately 1 to 3 per stem.

*Peduncle.*—Straight, rigid, it bears many glandular aciculas, its length is approximately 3 to 3.5 cm. on average.

*Sepals.*—Upper surface: tormentose, greenish colored with glandular edges. Under surface: medium green, more or less glandular, the outside sepals have edges which are slightly appendiculated.

*Buds.*—Shape: globular. Length: approximately 1.5 cm. on average. Size: small. Color upon opening: Upper Surface: white, White Group 155A, edges with bengal rose, Red-Purple Group 57B. Under surface: creamy white, White Group 155A, lightly edged and shaded with light bengal rose, Red-Purple Group 57D.

*Flower.*—Form: initially as a cup with a hollow center and subsequently as an umbrella. Diameter: approximately 4 to 4.5 cm. on average. Color (when opening begins): Upper surface: white, White Group 155A, edged with bengal rose, Red-Purple Group 57B. Under surface: creamy white, White Group 155A, slightly edged and shaded with light bengal rose, Red-Purple Group 57D. Color (when blooming): Upper surface: white, White Group 155A, edged with bengal rose, Red-Purple Group 57B. Under surface: creamy white, White group 155A, slightly edged and shaded with light bengal rose, Red-Purple Group 57D. Color (at end of opening): Upper surface: white, White Group 155A, edged with bengal rose, Red-Purple Group 57B, and more or less widely shaded with bengal rose, Red-Purple Group 57C. Under surface: creamy white, White Group 155A, edged and more or less suffused with bengal rose, Red-Purple Group 57C and 57D. Fragrance: none. Lasting quality: long. Petal number: approximately 80 to 85 on average. Petal form: generally flattened on the outside and oval to elliptical on the inside. Petal texture: firm. Petal drop: good. Anthers: normal, ochre. Stamen number: approximately 40 to 45 on average. Filaments: free, straw colored, of irregular heights. Pistil number: approximately 26 to 30 on average. Stigmas: normal, straw colored. Style: straw colored with a fuchsine tip, of irregular heights. Receptacle: medium green at the dehiscence of the anthers and in longitudinal section it is narrow and pear shaped.

Development:

*Vegetation.*—Vigorous.

*Blooming.*—Abundant and continuous.

*Aptitude to bear fruit.*—Slight to none.

*Resistance to disease.*—Very good.

It is claimed:

1. A new and distinct variety of Miniature rose plant characterized by the following combination of characteristics:

(a) forms in abundance on a continuous basis attractive very double bicolored blossoms which are white with bengal rose edges, have small central petals, and assume an umbrella configuration when fully open, (b) exhibits a bushy growth habit, and (c) forms glossy foliage;

substantially as herein shown and described, together with the parts thereof.

* * * * *